(12) United States Patent
Takaoka

(10) Patent No.: US 7,018,630 B2
(45) Date of Patent: Mar. 28, 2006

(54) BACILLUS NATTO CULTURE EXTRACT

(75) Inventor: Shinsaku Takaoka, Kuse-gun (JP)

(73) Assignee: Japan Bio Science Laboratories, Inc., Osaka (JP)

( * ) Notice: Subject to any disclaimer, the term of this patent is extended or adjusted under 35 U.S.C. 154(b) by 2 days.

(21) Appl. No.: 10/761,430

(22) Filed: Jan. 22, 2004

(65) Prior Publication Data

US 2004/0209333 A1    Oct. 21, 2004

Related U.S. Application Data

(63) Continuation of application No. 10/060,658, filed on Jan. 30, 2002, now Pat. No. 6,730,504, which is a continuation of application No. 09/832,595, filed on Apr. 11, 2001, now abandoned.

(30) Foreign Application Priority Data

Apr. 21, 2000   (JP)   .............................. 2000-120539

(51) Int. Cl.
   *C12P 7/66*    (2006.01)
   *A23K 1/28*    (2006.01)
   *A61K 38/45*   (2006.01)

(52) U.S. Cl. .................... 424/94.5; 435/71.1; 435/194; 424/61; 424/439; 424/441; 424/451; 424/464; 424/480

(58) Field of Classification Search ............... 435/71.1, 435/194; 424/94.5, 439, 441, 451, 464, 480; 426/61
   See application file for complete search history.

(56) References Cited

U.S. PATENT DOCUMENTS

| | | | |
|---|---|---|---|
| 6,420,145 B1 | 7/2002 | Sumi | |
| 6,537,543 B1 | 3/2003 | Minakawa | |
| 6,669,971 B1 | 12/2003 | Kato et al. | |
| 6,730,504 B1 * | 5/2004 | Takaoka | ..................... 435/183 |

OTHER PUBLICATIONS

Sumi et al., "A Novel Fibrinolytic Enzyme (nattokinase) in the Vegetable Cheese Natto; a typical and popular soybean food in the Japanese diet," *Experientia*, 1987, pp. 1110-1111, vol. 43, Birkhauser Verlag, CH-4010 Basel/Switzerland.

Sumi et al., "Enhancement of the Fibrinolytic Activity in Plasma by Oral Administration of Nattokinase," *Acta Haematol*, 1990, pp. 139-143, vol. 1990, S. Karger AG, Basel, Switzerland.

Nishimura et al., "Natto diet was apparently effective in a case of incipient central retinal vein occlusion," *Ganka Rinsho Ihou*, 1994, pp. 53-57, vol. 88, No. 9 (partial translation provided).

Sumi et al., "A Novel Strong Fibrinolytic Enzyme (Nattokinase) in the Vegetable Cheese "Natto", " *Fibrinolysis, International Journal of Fibrinolysis and Thrombolysis*, 1988, p. 67, vol. 2, Suppl. 1, TNO Corporate, The Netherlands, Dr. C. Kluft and Dr. F. Haverkate, Eds.

Computer WPIDS Derwent Abstract 1996-42191313[42] JP08208512, Aug. 18, 1996.

Suzuki et al., "Dietary supplementation of fermented soybean, natto, suppresses intimal thickening and modulates the lysis of mural thrombi after endothelial injury in rat femoral artery," *Life Sciences*, 2003, pp. 1289-1298, vol. 73, Elsevier Science Inc.

Anthony, "Soy and Cardiovascular Disease: Cholesterol Lowering and Beyond," *J. Nutr.*, 2000, pp. 662S-663S, vol. 130, American Society for Nutritional Sciences.

Ichishima et al., "Spore Fatty Acid Composition in *Bacillus natto*, A Food Microorganism," *Food Chemistry*, 1982, pp. 1-9, vol. 8, Applied Science Publishers Ltd., England.

Sumi et al., "Fibrinolytic Effect on the Japanese Traditional Food "Natto" (Nattokinase)," http://www.jafra.gr.jp/sumi4-e.html (*Thromb. Haemostas*, 1989, p. 549, vol. 62).

Fujita et al., "Purification and Characterization of a Strong Fibrinolytic Enzyme (Nattokinase) in the Vegetable Cheese Natto, a popular Soybean Fermented Food in Japan," *Biochemical and Biophysical Research Communications*, Dec. 30, 1993, pp. 1340-1347, vol. 197, No. 3.

Maruyama et al., "Effect of Natto Diet on Blood Pressure," http://www.jafra.gr.jp/sumi5-e.html (*Basic and Clinical Aspects of Japanese Traditional Food Natto II*, 1998, 1-3).

* cited by examiner

*Primary Examiner*—Herbert J. Lilling
(74) *Attorney, Agent, or Firm*—Foley & Lardner LLP

(57) ABSTRACT

A *Bacillus natto* culture is treated with chitosan, and then filtered, concentrated, and dried. According to this method, a *Bacillus natto* culture extract containing nattokinase and 1 µg or less of vitamin K2/g dry weight is obtained.

22 Claims, No Drawings

BACILLUS NATTO CULTURE EXTRACT

This application is a continuation of Ser. No. 10/060,658, filed Jan. 30, 2002 now U.S. Pat. No. 6,730,054, which also is a continuation of Ser. No. 09/832,595, filed Apr. 11, 2001 now abandoned, and the contents of both of these parent applications are incorporated by reference herein in their entireties.

BACKGROUND OF THE INVENTION

1. Field of the Invention

The present invention relates to a food product containing a thrombolytic enzyme, nattokinase, but containing little or none of a blood coagulation factor, vitamin K2.

2. Description of the Prior Art

The *Bacillus natto* was discovered by Sumi et al. to produce the thrombolytic enzyme nattokinase (Experientia Vol. 43, p. 1110 (1987)), and thus the nutritional value of natto and its value as a health food are looked at again. It is known that nattokinase itself acts as a fibrinolytic enzyme, and lyses thrombi when ingested as a food. Nattokinase has extremely good characteristics such as having a long half life and retaining its effectiveness for a long period of time. In addition, it is reported that urokinase having the same thrombolytic activity as nattokinase does not clearly have a therapeutic effect on incipient central retinal vein occlusion, but that this effect can be clearly seen with nattokinase (Nishimura et al., Ganka Rinsho Ihou (in Japanese), Vol. 88, No. 9, pp. 53–57 (1994)).

Accordingly, food products containing large amounts of nattokinase, for example, powders and capsules formed from *Bacillus natto* culture extract, are being marketed as health foods.

On the other hand, the *Bacillus natto* is known to produce large amounts of vitamin K2. Vitamin K2 is known as an essential component of the blood coagulation system. Further, vitamin K2 has other physiological functions, and is said to cause absorption disorders in newborns and osteoporosis in the elderly when it is deficient, and said to cause hemolytic anemia, splenomegaly, nephropathy, hepatopathy and the like when it is present in excess. Thus, a *Bacillus natto* culture extract simultaneously contains nattokinase as a thrombolytic system effector and vitamin K2 as a blood coagulation system effector.

The necessary daily intake of vitamin K2 for adults is generally 55 to 65 µg. Large amounts of vitamin K's are found in foods such as seaweed, broccoli and the like. Because vitamin K's are also produced by enterobacteria and by *Bacillus natto* that grow in the intestines when natto is ingested, it is possible for vitamin K2 to be produced. Therefore, it is said that the necessary intake of vitamin K2 can be satisfied by a normal diet. Thus, it is generally not necessary to supplement vitamin K2.

On the other hand, problems occur with patients who are administering synthetic inhibitors of the vitamin K-dependent blood coagulation factors (for example, protothrombin VII, IX, X and the like) to prevent thrombosis. When these patients ingest a natto or a *Bacillus natto* culture extract containing the thrombolytic enzyme, nattokinase, in order to prevent thrombosis and the like, they also ingest vitamin K2 at the same time, and the effect of synthetic inhibitor of the vitamin K-dependent blood coagulation factor is counteracted.

Accordingly, in order to prevent thrombogenesis, a food product of *Bacillus natto* culture extract in which the vitamin K2 content has been reduced are desired, and therefore, methods of reducing vitamin K2 in the food product have been attempted. Using organic solvents such as hexane to extract fat-soluble vitamin K2 is one of these methods.

However, the problems with this method are: fat-soluble nutrients are also extracted and removed in addition to vitamin K2: the need to remove organic solvents such as hexane leads to problems in terms of a production technique such as an increase in the cost of production; consumer opposition to the use of organic solvents; and the possibility that organic solvents remain in the food.

Accordingly, a *Bacillus natto* culture extract in which the vitamin K2 content has been reduced is in demand, as well as a method in which vitamin K2 can be simply and easily extracted without using organic solvents.

SUMMARY OF THE INVENTION

The present invention was put into practice for the purpose of solving the aforementioned problems, and provides a *Bacillus natto* culture extract containing nattokinase and an amount of vitamin K2 below a specified level, and a method for producing the same. According to the present invention, the problems with the food products containing nattokinase of the prior art are solved. Therefore, an optimal diet that nutrients are excellent, the activity of nattokinase is enhanced, and there are no longer any concerns about the excessive intake of vitamin K2, is provided. Furthermore, because little or none of the blood coagulation factor, vitamin K2, is present, an optimal diet for patients with diseases of the blood coagulation system is also provided.

The present invention relates to a *Bacillus natto* culture extract containing nattokinase and 1 µg or less of vitamin K2/g dry weight (hereinafter referred to as the *Bacillus natto* culture extract of the present invention).

In a preferred embodiment, the *Bacillus natto* culture extract of the present invention is obtained by a method which comprises culturing natto in a liquid culture medium, and treating the culture medium obtained therefrom with chitosan.

In a preferred embodiment, the *Bacillus natto* culture extract is in the form of a concentrated extract, a paste, a powder, a granule, a capsule, a drinkable preparation (beverage) or a tablet.

In addition, the present invention relates to a method for producing a *Bacillus natto* culture extract containing nattokinase and 1 µg or less of vitamin K2/g dry weight, comprising culturing natto in a liquid culture medium to obtain a cultured medium, and treating the cultured medium with chitosan.

Further, the present invention relates to a method for collecting vitamin K2, comprising treating a sample containing vitamin K2 with chitosan, and extracting the vitamin K2 adsorbed by the chitosan with an organic solvent.

According to the present invention, a *Bacillus natto* culture extract containing nattokinase and a concentration of 1 µg or less of vitamin K2/g dry weight can be obtained by a simple and easy method using chitosan. Because it contains an exceedingly small amount of vitamin K2, this *Bacillus natto* culture extract can prevent thrombogenesis and the excessive intake of vitamin K2 in healthy individuals, and is an excellent food product that allows people who limit their intake of vitamin K2 to safely ingest nattokinase.

These and other advantages of the present invention will become apparent to those skilled in the art upon reading and understanding the following detailed description.

DETAILED DESCRIPTION OF THE INVENTION

The *Bacillus natto* culture extract of the present invention contains nattokinase and 1 µg or less of vitamin K2/g dry weight. Preferably, it contains 0.5 µg or less of vitamin K2/g dry weight, and more preferably contains 0.1 µg or less of vitamin K2/g dry weight.

The form of the *Bacillus natto* culture extract includes a culture medium itself obtained by culturing the *Bacillus natto*, completely removing the bacteria from the liquid culture medium, and almost completely or completely removing the vitamin K2 from the culture medium. It is possible for the *Bacillus natto* culture extract to be in the form of a liquid, a powder, or a solid. For example, a liquid can include a concentrated extract of the culture medium and a paste. A powder can include a dried powder, a granule obtained by further drying a concentrated extract or a paste, and the like. For example, a solid can be a tablet obtained by compressing. The tablet can be coated depending on a variety of uses, including a sugar-coated tablet. Alternatively, the concentrated extract, paste, powder or granule can be contained in a capsule. Further, it can be in the form of a drinkable preparation, such as a beverage.

The *Bacillus natto* culture extract of the present invention contains nattokinase. The nattokinase content is not limited, however, it is preferable to be 20 FU/g or more, more preferably 1000 FU/g or more, and even more preferably 2500 FU/g or more. These are variable according to concentration of the *Bacillus natto* culture extract of the present invention. With dry powder, the aforementioned concentration can increase to 5000 FU/g or more, or 10000 FU/g or more. For example, according to the method reported in by Sumi et al in Experientia, Vol. 43, p. 1110 (1987), the nattokinase activity can be detected by a clear plaque formed on a fibrin plate. In addition, in the present invention, nattokinase means an enzyme that is produced by the *Bacillus natto* and has the ability to form a clear plaque on a fibrin plate.

The vitamin K2 contained in the *Bacillus natto* culture extract of the present invention can be 1 µg/g dry weight or less, and can be at the lower limit for detection (0.001 µg/g dry weight) or less. The removal of vitamin K2 is carried out using chitosan. The method of removal will be explained below. By means of this chitosan treatment, 99% or more of the vitamin K2 can be removed from the culture medium.

Below, the so-called *Bacillus natto* (typically, *Bacillus subtilis natto*) will be offered as an example to explain the method for producing the *Bacillus natto* culture extract of the present invention. In addition, in this explanation, the numerical value of vitamin K2 and the like will vary with the type of *Bacillus natto* used, the condition of culture and the like, and the present invention is not limited thereby.

The microorganisms used in the production of the *Bacillus natto* culture extract are classified as *Bacillus natto*. Any microorganisms that can produce nattokinase can be used, including *Bacillus natto* isolated from commercially available natto.

The culture medium used in cultivation of *Bacillus natto* is not limited, however, it is preferable to choose the medium by considering that the concentrated culture medium itself will become a food product. As a culture medium for culturing *Bacillus natto*, carbon sources such as starch (for example, corn starch), glucose, sucrose, nitrogen sources such as defatted soybeans, meat extract, inorganic salts such as calcium carbonate, magnesium chloride, and, if necessary, fatty acids and the like, are used. It is preferable that the components of the medium are food additive grade.

The method for culturing *Bacillus natto* is not limited. However, it is preferable to culture *Bacillus natto* with aeration and agitation for large scale cultivation. The culture temperature is not limited so long as *Bacillus natto* can grow. However, 30 to 45° C. is preferable, 32 to 42° C. is more preferable, and approximately 37° C. is most preferable. It is preferable that the culture period be 3 to 4 days.

Generally, the supernatant of the culture medium obtained (hereinafter referred to as "cultured medium") has nattokinase activity of approximately 300 to 600 FU/ml, and contains approximately 10 to 100 µg of vitamin K2/g dry weight. This culture product is brought into contact with chitosan, and the vitamin K2 is adsorbed by the chitosan. The chitosan may be in solution or solid form, preferably an aqueous solution of chitosan may be added.

With the chitosan treatment, when treating the cultured medium with chitosan alone, it is preferable that a chitosan aqueous solution containing a chitosan of 0.1 to 1% by weight (hereinafter, wt %) is used. A preferable chitosan concentration is 0.2 to 0.8 wt %, and more preferably 0.3 to 0.6 wt %. When chitosan alone does not dissolve in a water, the pH of the aqueous solution can be acidified so that it can dissolve. When its use as food is considered, it is more preferable to use an aqueous chitosan solution in which 0.05 to 1 wt %, and preferably 0.1 to 0.3 wt %, of acetic acid has been added (a chitosan-acetic acid solution).

With respect to the cultured medium, 1 to 10 wt % of the aforementioned aqueous chitosan solution or the chitosan-acetic acid solution, preferably 5 to 10 wt %, and more preferably 6 to 8 wt %, is added thereto and allowed to react sufficiently with stirring. Then, for example, a filter aid such as perlite, diatomaceous earth is used, and the culture medium is filtered with a pressurized-type filtration device to give a clear filtrate. Alternatively, after the aqueous chitosan solution or the chitosan-acetic acid solution is added to the cultured medium, a filter aid such as perlite, diatomaceous earth is added thereto, the cultured medium is stirred for an appropriate time, and then filtered with a pressurized-type filtration device to give a filtrate. The chitosan treatment in the present specification is not limited to the methods described above. Chitosan and the cultured medium can be simply brought into contact with each other.

In addition, the chitosan dissolved in the aqueous solution adsorbs the bacterial cells in the cultured medium, is removed by the filter aid, and is almost not present in the filtrate. By the aforementioned chitosan treatment, 99% or more, and occasionally 99.9% or more, of the vitamin K2 in the filtrate is removed.

The filtrate thus obtained or further filtrated using filter aid is concentrated by using a concentrator such as a reverse osmosis concentrator. The majority of compounds having a molecular weight of 100 or less can be removed by using this reverse osmosis concentrator. Further, a concentrate of the *Bacillus natto* culture medium is obtained as needed by aseptic filtration using, for example, a 0.5 µm and/or 0.2 µm membrane filter. At this point, the concentration of vitamin K2 in the filtrate is 1 µg dry weight or less.

The concentrate thus obtained will become paste-like by further concentration. Further, the appropriate food additives such as water-soluble dietary fiber, lactose, cellulose are added to the concentrate thus obtained to produce a powder form and a granular form of the *Bacillus natto* culture extract by freeze-drying. In addition, the concentrate, paste, powder, and granular forms of the extract can be encapsuled to produce capsules containing the *Bacillus natto* culture extract. Tablets can also be produced. The tablets can be coated depending on a variety of uses, including sugar-coated tablets.

On the other hand, a crude product containing vitamin K2 can be obtained by extracting it from the filtration residue in the chitosan treatment with an organic solvent such as lower alcohol, hexane, ethyl ether, acetone, ethyl acetate or a combination thereof, and then concentrating it. A preferable mixture of solvents is hexane-isopropyl alcohol (3:2 ratio by weight). To recover vitamin K2 from this product, standard methods usually used by those skilled in the art such as molecular distillation, steam distillation are applied. The recovered vitamin K2 can be used in medical treatments or prevention of osteoporosis.

The activity of nattokinase and the amount of vitamin K2 are measured according to the method described below.

(A: Measurement of Nattokinase Activity)

Nattokinase acts upon fibrin, and thus nattokinase activity is measured by an increase in the amount of acid-soluble low molecular weight degradation products with decomposition of fibrin. This increase is determined by measuring the absorbance of ultraviolet (275 nm).

(a-1: Preparation of an Aqueous Fibrinogen Solution)

Seventy-two mg of fibrinogen (Sigma Corp., fibrinogen fraction I derived from bovine blood plasma, Type I-S) is dissolved in 10 ml of 50 mM borax buffer (pH 8.5, 150 mM NaCl) to prepare a 0.72% (w/v) aqueous fibrinogen solution.

(a-2: Preparation of a Thrombin Solution)

Thrombin (Sigma Corp., derived from bovine blood plasma) is dissolved in 50 mM borax buffer so as to have a concentration of 1000 U/ml. When this solution is to be used, it is diluted 50 times with the borax buffer (i.e., 20 U/ml).

(a-3: Activity Measurement)

First, 1.4 ml of 50 mM borax buffer and 0.4 ml of aqueous fibrinogen solution are placed into a test tube, and then warmed at 37° C.+−0.3° C. in the water bath for five minutes. Then, 0.1 ml of the thrombin solution is added thereto, and the mixture is stirred. This mixture is allowed to stand in the water bath for 10 min. Then, 0.1 ml of a sample solution is added to the mixture, the mixture is stirred for 5 sec., and then allowed to stand in the water bath. The mixture is stirred for 5 sec. at 20 min. and 40 min. after adding the sample solution. At 60 min. after adding the sample solution, 2 ml of 0.2M trichloroacetate solution is added thereto, the mixture is stirred, and allowed to stand for an additional 20 min. The reaction mixture is centrifuged for 5 min. at 15,000×g, and the absorbance (Ar) of the supernatant at 275 nm is measured.

As a control, 1.4 ml of 50 mM borax buffer and 0.4 ml of aqueous fibrinogen solution are placed into a test tube, and then warmed at 37° C.+−0.3° C. in the water bath for five minutes. Then, 0.1 ml of the thrombin solution is added, and the mixture is stirred. This mixture is allowed to stand in the water bath for 10 min. Then, 2 ml of 0.2M trichloroacetate solution is added thereto and stirred. Next, 0.1 ml of the sample solution is added to the mixture and stirred, and allowed to stand for 20 min. The reaction mixture is centrifuged for 5 min. at 15,000×g, and the absorbance (Ac) of the supernatant at 275 nm is measured.

Nattokinase activity is determined according to the formula below.

$$A(FU/ml)=\{(Ar-Ac)/(0.01\times 60\times 0.1)\}\times D,$$

where D is the dilution ratio.

(B: Quantifitation of Vitamin K2)

Vitamin K2 is measured by HPLC, and a sample prepared according to the following method is used therein.

(b-1: Preparation of a Sample for Use in HPLC)

First, 0.5 ml of the sample to be measured, 0.5 ml of water, and 1.5 ml of isopropyl alcohol are mixed and stirred, and then 5 ml of hexane is added thereto, and stirred. The mixture is centrifuged at 1,700×g for 10 min. at 20° C., to give 4 ml of the supernatant (organic layer). The supernatant is concentrated, dried, and then dissolved in 100 μl of ethanol to give the sample solution.

(b-2: HPLC Conditions)

The HPLC conditions are as follows.

Column: Simadzu STR ODS-2 4.6×250 mm

Eluate: 97% ethanol

Flow rate: 0.7 ml/min.

Detection: UV 254 nm

Under these conditions, the retention time of vitamin K2 is the latter half of 16 min.

EXAMPLES

The following examples are provided to explain the present invention. However, the present invention is not limited thereby.

Examples 1–2 and Comparative Examples 1–2

A culture medium at pH 7.0 containing 1 wt % of polypeptone, 1 wt % of glucose, 0.5 wt % of meat extract, and 0.2 wt % of NaCl was placed into a round bottom flask, inoculated with *Bacillus natto*, and then cultured at 37° C. for 18 hours. The culture medium obtained therefrom was inoculated into a seed culture tank containing the same culture medium composition, and cultured for 22 hours to give a seed culture.

A culture medium at pH 7.3 containing 6.25 wt % of corn starch, 3.09 wt % of defatted soybeans, 0.15 wt % of food additive grade calcium carbonate, 1.5 wt % of soybean oil, and 0.008% of silicon was prepared. To the culture medium, the aforementioned seed culture was added, and then cultured for 69 hours at 37° C. with aeration of 0.5 VVM. The culture medium obtained (cultured medium) contained 470 FU/ml of nattokinase and 55 μg of vitamin K2 per gram of the cultured medium.

Then, 15 kg of an aqueous chitosan solution containing 0.4 wt % of chitosan (Kyowa Technos) and 0.18 wt % of acetic acid was added to a portion of the cultured medium, here 200 L, and then 5 kg of perlite was added, and stirred (Example 1). Independently, 15 kg of the aqueous chitosan solution alone was added to another 200 L of the cultured medium and stirred (Example 2). To another 200 L of the cultured medium, either 5 kg of perlite (brand name: Topco perlite; produced by Nihon Kouken Corp.) was added (Comparative Example 1), or 5 kg of diatomaceous earth (brand name: Celite #505, manufactured by Celite Corporation: Lompoc, Calif. 93438-0519 USA) was added (Comparative Example 2). Each cultured medium was stirred for one hour, and then filtered by a pressurized-type filtration device to obtain a filtrate. In addition, in filtration process in Example 2, diatomaceous earth was used as a filter aid. The amount of vitamin K2 in each filtrate was measured, and the results are shown in Table 1.

TABLE 1

| | | Vitamin K2 (μg/g cultured medium) | | Filtration |
| | Filter Aid | Before Filtration | After Filtration | Percentage (%) |
|---|---|---|---|---|
| Example 1 | Chitosan-Perlite | 55 | 0.002 | 99.99 |
| Example 2 | Chitosan solution | 55 | 0.15 | 99.72 |
| Comparative Example 1 | Perlite | 55 | 54 | 1.8 |
| Comparative Example 2 | Diatomaceous Earth | 55 | 55 | 0 |

As is apparent from Table 1, almost all of the vitamin K2 in Examples 1 and 2 was removed by treating with the chitosan solution. That is, with the chitosan-perlite combination, 99.9% of the vitamin K2 was removed. With chitosan only, 99.72% of the vitamin K2 was removed. When only perlite was used (Comparative Example 1) and when only diatomaceous earth was used (Comparative Example 2), little vitamin K2 was removed.

Example 3

First, 5 kg of diatomaceous earth was added to 180 L of the filtrate (chitosan—perlite treatment) obtained in Example 1. This mixture was precisely filtered in a pressurized-type filtration device, and then concentrated to 35 L by using reverse osmosis membrane. This concentrate was passed through a 0.2 μm membrane filter to obtain a Bacillus natto culture extract. Then, 0.2 kg of water-soluble dietary fiber was added to 5 L of this Bacillus natto culture extract. This mixture was freeze-dried, and powdered to give approximately 800 g of Bacillus natto culture extract powder. The contents of nattokinase and vitamin K2 in the Bacillus natto culture extract thus obtained and its powder are shown in Table 2. In addition, 22 different varieties of commercially available natto were purchased as a comparison, and the contents of nattokinase and vitamin K2 in about 50 g of these natto's are collectively shown in Table 2.

TABLE 2

| Product | Nattokinase Activity (FU/g) | Vitamin K2 (μg/g dry weight) |
|---|---|---|
| Bacillus natto culture extract | 2500 | 0.01 |
| Bacillus natto culture extract powder | 13000 | 0.05 |
| Commercially available natto | 20–40 | 6–12 |

As shown in Table 2, the Bacillus natto culture extract and its powder having a high level of nattokinase activity and 0.1 μg or less of vitamin K2/g dry weight can be obtained according to the present invention. In particular, the usefulness of the extract of the present invention is apparent when compared to commercially available natto. One pack of commercially available natto (approximately 50 g) contains 1000 to 2000 FU of nattokinase and 300 to 600 μg of vitamin K2. That is, commercially available natto contains only 20 to 40 FU of nattokinase per gram, but the Bacillus natto culture extract and its powder contain 2500 FU and 13,000 FU of nattokinase per gram, respectively. There is approximately 60 to 120 times and approximately 300 to 600 times more, respectively, of nattokinase in the Bacillus natto culture extract and its powder of the present invention than that found in commercially available natto.

Moreover, with respect to commercially available natto that contains 6 to 12 μg of vitamin K2/g, the Bacillus natto culture extract and its powder of the present invention contain only 0.01 μg and 0.05 μg, respectively. That is, the Bacillus natto culture extract and its powder of the present invention contain only approximately {fraction (1/500)}th and {fraction (1/1000)}th, respectively, of the vitamin K2 contained in the commercially available natto.

In addition, vitamin K2 can be added as necessary to the Bacillus natto culture extract obtained (the concentrated extract, paste, powder, and granule) to give the Bacillus natto culture extract enriched with vitamin K2. For example, the Bacillus natto culture extract can be combined with vitamin K2 in an appropriate ratio so as to have the nattokinase activity of 1000 to 2000 FU that is in one pack (about 50 g) of commercially available natto, and contain 55 to 65 μg of vitamin K2 needed daily by an adult. Then, the combination is formed into capsules, tablets, drinkable preparations (beverages), and the like. Vitamin K2 can also be obtained by the method of Example 4 discussed below.

Example 4

The residue generated by the production process of Example 1 (chitosan—perlite treatment) was collected. Then, 750 g of hexane and 500 g of isopropyl alcohol were added to 500 g of the collected residue and stirred well. The organic layer was collected by decantation. In the organic layer, 120 μg of vitamin K2/g was contained. Then, the organic layer was evaporated to dryness (60° C.) to collect 150 mg of purified vitamin K2.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method of administering nattokinase to a patient restricting his or her intake of vitamin K2 or for whom vitamin K2 is contraindicated, comprising administering to said patient a composition comprising a Bacillus natto culture extract comprising nattokinase and 1 μg or less of Vitamin K2/g dry weight.

2. The method of claim 1, wherein the composition is in the form of a liquid, a paste, a powder, a granule, a solid, or a freeze-dried solid.

3. The method of claim 1, wherein the composition is in the form of a capsule or tablet.

4. The method of claim 1, wherein the composition is a food product.

5. The method of claim 1, wherein the composition further comprises one or more additives selected from the group consisting of water-soluble dietary fiber, lactose, and cellulose.

6. The method of claim 1, wherein the extract comprises at least 1000 FU/g nattokinase.

7. The method of claim 1, wherein the extract comprises at least 2500 FU/g nattokinase.

8. The method of claim 1, wherein the extract comprises at least 5000 FU/g nattokinase.

9. The method of claim 1, wherein the extract comprises at least 10,000 FU/g nattokinase.

10. The method of claim 1, wherein the Bacillus natto culture extract is obtained from a Bacillus natto culture broth prepared by a process comprising (i) culturing *Bacillus natto* in a liquid medium to produce a cultured medium comprising nattokinase and vitamin K2 and (ii) treating the cultured medium with chitosan to substantially remove vitamin K2 therefrom while retaining other nutrients.

11. A method of administering nattokinase to a patient at risk of or suffering from thrombogenesis, comprising administering to said patient a composition comprising a *Bacillus natto* culture extract comprising nattokinase and 1 μg or less of Vitamin K2/g dry weight.

12. The method of claim 11, wherein the composition is in the form of a liquid, a paste, a powder, a granule, a solid, or a freeze-dried solid.

13. The method of claim 11, wherein the composition is in the form of a capsule or tablet.

14. The method of claim 11, wherein the composition is a food product.

15. The method of claim 11, wherein the composition further comprises one or more additives selected from the group consisting of water-soluble dietary fiber, lactose, and cellulose.

16. The method of claim 11, wherein the extract comprises at least 1000 FU/g nattokinase.

17. The method of claim 11, wherein the extract comprises at least 2500 FU/g nattokinase.

18. The method of claim 11, wherein the extract comprises at least 5000 FU/g nattokinase.

19. The method of claim 11, wherein the extract comprises at least 10,000 FU/g nattokinase.

20. The method of claim 11, wherein the *Bacillus natto* culture extract is obtained from a *Bacillus natto* culture broth prepared by a process comprising (i) culturing *Bacillus natto* in a liquid medium to produce a cultured medium comprising nattokinase and vitamin K2 and (ii) treating the cultured medium with chitosan to substantially remove vitamin K2 therefrom while retaining other nutrients.

21. The method of claim 11, further comprising administering to the patient a synthetic inhibitor of a vitamin K-dependent blood coagulation factor.

22. A method of administering nattokinase to a patient in need thereof, comprising administering to said patient a composition comprising a *Bacillus natto* culture extract obtained from a chitosan-treated *Bacillus natto* culture broth that comprises nattokinase and 1 μg or less of Vitamin K2/g dry weight and that is prepared by a process comprising (i) culturing *Bacillus natto* in a liquid medium to produce a cultured medium comprising nattokinase and vitamin K2 and (ii) treating the cultured medium with chitosan to substantially remove vitamin K2 therefrom while retaining other nutrients.

* * * * *